(12) United States Patent
Prins et al.

(10) Patent No.: US 10,543,217 B2
(45) Date of Patent: Jan. 28, 2020

(54) METHOD OF TREATING FRAILTY

(75) Inventors: Marjanna Prins, Arnhem (NL); Helenius Jan Kloosterboer, Oss (NL)

(73) Assignee: Organext Research B.V., Arnhem (NL)

( * ) Notice: Subject to any disclaimer, the term of this patent is extended or adjusted under 35 U.S.C. 154(b) by 0 days.

(21) Appl. No.: 13/318,650

(22) PCT Filed: Aug. 23, 2010

(86) PCT No.: PCT/NL2010/050524
§ 371 (c)(1),
(2), (4) Date: Dec. 19, 2011

(87) PCT Pub. No.: WO2011/025368
PCT Pub. Date: Mar. 3, 2011

(65) Prior Publication Data
US 2012/0196837 A1 Aug. 2, 2012

(30) Foreign Application Priority Data
Aug. 24, 2009 (EP) .................................. 09168522

(51) Int. Cl.
*A61K 31/56* (2006.01)
(52) U.S. Cl.
CPC .................................. *A61K 31/56* (2013.01)
(58) Field of Classification Search
CPC ....... A61K 23/00; A61K 31/56; A61K 31/592
USPC ........................................................ 514/167
See application file for complete search history.

(56) References Cited

U.S. PATENT DOCUMENTS

| | | | | |
|---|---|---|---|---|
| 4,308,264 A | * | 12/1981 | Conway et al. | 514/167 |
| 5,898,038 A | * | 4/1999 | Yallampalli et al. | 514/742 |
| 6,031,000 A | * | 2/2000 | Nissen | A61K 31/195 514/557 |
| 6,133,320 A | * | 10/2000 | Yallampalli et al. | 514/632 |
| 6,509,326 B1 | * | 1/2003 | Andon | A23L 2/39 514/167 |
| 7,576,053 B2 | * | 8/2009 | Masuda | A61K 31/202 514/1.1 |
| 8,426,391 B2 | * | 4/2013 | Bishop | A61K 9/0019 514/167 |
| 8,795,693 B2 | * | 8/2014 | Tamarkin | A61K 9/122 424/401 |
| 8,814,820 B2 | * | 8/2014 | Bergheim | A61F 9/0017 604/10 |
| 9,066,958 B2 | * | 6/2015 | Vieth | A23D 9/007 |
| 9,101,662 B2 | * | 8/2015 | Tamarkin | A61K 9/122 |
| 9,259,430 B2 | * | 2/2016 | Rathmacher | A61K 31/59 |
| 2003/0198689 A1 | * | 10/2003 | Arata | A01N 59/16 424/618 |

FOREIGN PATENT DOCUMENTS

EP    1464979    2/1977

OTHER PUBLICATIONS

Hedstrom et al. (Journal of Bone and Joint Surgery (Br.), vol. 84-B, No. 4, May 2002, pp. 497-503.*
Ming Teng et al. (J Am Soc Nephrol 16: 1115-1125, 2005).*
http://www.mgh.harvard.edu/ (Published on Feb. 28, 2005 at 6:09 PM).*
Bagchus et al. (J. Clin. Endocrinol. Metab, May 2005, 90(5):2524-2630).*
EPO European priority application No. 09168522.2, the Extended European Search Report and the European Search Opinion, 8 pages, dated Mar. 25, 2010.
Kicman, A T, "Pharmacology of anabolic 1-25 steroids" British Journal of Pharmacology, vol. 154, No. 3, Jun. 2008 (Jun. 2008), pp. 502-521, XP002574979.
Hedstrom, M. et al. "Positive effects of anabolic steroids, vitamin D and calcium on muscle mass, bone mineral density and clinical function after a hip fracture. A randomised study of 63 women" The Journal of Bone and Joint Surgery, British Volume, vol. 84, No. 4, May 2002, pp. 497-503, XP002574974.
Lyritis, George P. et al. "Effect of nandrolone decanoate and 1-alpha-hydroxy-calciferol on patients with vertebral osteoporotic collapse. A double-blind clinical trial" Bone and Mineral, vol. 27, No. 3, Jan. 1, 1994, pp. 209-217, XP022641723.
Sheffield-Moore, Melinda et al. "Androgen therapy induces muscle protein anabolism in older women" Journal of Clinical Endocrinology & Metabolism, vol. 91, No. 10, Oct. 2006, pp. 3844-3849, XP002574975.
Schroeder, E. Todd et al. "Six-week improvements in muscle mass and strength during androgen therapy in older men" Journals of Gerontology, Series A, Biological Sciences and Medical Sciences, Washington, DC, US, vol. 60, No. 12, Dec. 1, 2005, pp. 1586-1592, XP009131317.
Campbell, Stephen et al. "Pharmacological Treatment of Frailty in the Elderly" Journal of Pharmacy Practice and Research, vol. 39, No. 2, Jun. 2009, pp. 147-151, XP9131388.
Fried, Linda P. et al. "Frailty in older adults: evidence for a phenotype." The Journals of Gerontology. Series A, Biological Sciences and Medical Sciences, vol. 56, No. 3, Mar. 2001, pp. M146-M156, XP9131318.
PCT/NL2010/050524 International Search Report, 4 pages, dated Oct. 6, 2010.
International Preliminary Report on Patentability issued in corresponding application No. PCT/NL2010/050524 dated Feb. 28, 2012.

(Continued)

*Primary Examiner* — Sabiha N Qazi
(74) *Attorney, Agent, or Firm* — Morrison & Foerster LLP

(57) ABSTRACT

Disclosed is a method of treatment or prevention of frailty in an elderly patient, particularly having an age of 60 or older. The method provides the concomitant parenteral administration of a combination of an anabolic steroid and a vitamin D compound. A preferred combination comprises nandrolone decanoate and cholecalciferol (vitamin $D_3$). The invention, in a further preference, provides a booster therapy to support frail elderly that have undergone hospitalization or surgery to retain independence and regain their regular physical and mental activities.

12 Claims, 2 Drawing Sheets

(56) References Cited

OTHER PUBLICATIONS

Centers for Disease Control and Prevention, "Calcium and Bone Health," <http://www.cdc.gov/nutrition/everyone/basics/vitamins/calcium.html>, last updated Apr. 6, 2011.
Weisman, "The calcium connection to bone health across a woman's lifespan: a roundtable," *J. Reprod. Med.* 50:879-884, 2005.
PCT/NL2010/050524 International Search Report and Written Opinion, 14 pages, dated Oct. 6, 2010.
Bergink et al., "Comparison of the Receptor Binding Properties of Nandrolone and Testosterone Under In Vitro and In Vivo Conditions," *J. Steroid Biochem.*, 22(6):831-836 (1985).
Kicman, AT, "Pharmacology of anabolic steroids," British Journal of Pharmacology, 154:502-521 (2008).
Kloosterboer et al., "Combinatorial Effects of Nandrolone and Vitamin $D_3$ on Human Prostate LNCAP Cells," 94th annual meeting of The Endocrine Society in Houston, Texas (Jun. 23-26, 2012).
Montero-Odasso, et al., "Vitamin D in the aging musculoskeletal system: an authentic strength preserving hormone," Mol. Aspects Med., 26(3):203-219 (2005) (Abstract Only).
Overbeek and de Visser, "A Comparison of the Myotrophic and Androgenic Activities of the Phenylpropionates and Decanoates of Testosterone and Nandrolone," ACTA Endocrinologica, 38:285-292 (1961).

\* cited by examiner (a)

(b)

METHOD OF TREATING FRAILTY

CROSS REFERENCE TO RELATED APPLICATIONS

This application is a U.S. National Phase Application under 35 U.S.C. § 371 of International Application PCT/NL2010/050524, filed on Aug. 23, 2010, which claims the benefit of European Application No. 09168522.2, filed on Aug. 24, 2009, the entire contents of which are hereby incorporated by reference in their entireties.

FIELD OF THE INVENTION

The invention pertains to a method of treatment of frailty in an elderly patient. The invention also pertains to a pharmaceutical composition for use in such a method. The invention particularly pertains to a recovery booster therapy for frail elderly people.

BACKGROUND OF THE INVENTION

Frailty is a clinical syndrome with symptoms as low body weight due to unintentional weight loss, exhaustion, weakness, slow walking and low physical activity. Frailty is characterized by a decreased reserve and resistance to stressors, in turn resulting from cumulative decline across multiple physiologic systems, and causing a vulnerability to adverse outcomes. Increased insulin resistance, metabolic syndrome and osteoporosis mount among these.

A widely used definition of this complex geriatric syndrome, as proposed by Fried et al. (2001) *J Gerontol A Biol Sci Med Sci* 56:M146-M156, is based on an assessment of five distinct characteristics. An individual is considered to be frail if they possess at least three of the following five characteristics: unintentional weight loss in the past year; weakness of grip strength; poor endurance/exhaustion; slowness; and low physical activity level.

Frailty has been associated with changes in biomarkers like IL-6, CRP, 25-OH-vitamin-D, IGF-1, D-dimers and is in particular prominent in elderly people. In the context of the invention, elderly particularly have an age of 60 or older, and more particularly of 65 or older.

Frailty is associated with a gradual loss of efficient protein metabolism. In turn this affects metabolic rates, leading to syndromes as mentioned above.

A major aspect of frailty is that it affects muscle mass and strength, leading to increased incidence of falls and associated injuries like fractures and impaired mobility. Together with muscle mass related lower immunity, reduced healing rates and mental deterioration, this leads to a loss of independency.

Currently, no treatment has been registered specifically for the treatment of frailty. Some clinical investigation has been done on the effect of various treatments on individual frailty symptoms. This includes, e.g., the effect of anabolic steroids on muscle mass, which is well known to the skilled person.

A reference on the effect of the anabolic steroid oxandrolone on muscle mass in elderly men, is Schroeder et al. 2005 *J Gerontol A Biol Sci Med Sci* 60:1586-1592.

Low serum 25-OH-vitamin-D concentrations, which is a marker for calcitriol shortage, are commonly found in the elderly and are found to accompany the development of frailty symptoms.

A reference that advocates vitamin D therapy is Campbell and Szoeke, Journal of Pharmacy Practice and Research, vol. 39, no. 2, June 2009, 147-151 provides an overview of alternative pharmacological treatments of frailty in the elderly. One such treatment is that with vitamin D, which is referred to in respect of its effects on bone, muscle and balance. Another such treatment is with anabolic hormones, but this treatment is said to have no clear benefit in the frail elderly.

A reference on emerging therapies to treat frailty syndrome in the elderly, is Cherniack et al., Alternative Medicine Review Volume 12, Number 3 2007, pages 246-258. Herein the focus is on nutritional supplementation with e.g. vitamins, carotenoids, creatine, DHEA, or beta-hydroxy-beta-methylbutyrate, and on exercise modalities (tai chi and cobblestone walking). Supplementation with vitamin D is referred to as a promising means to alleviate components of frailty syndrome. Also, with reference to the vitamin D deficiencies frequently occurring in the elderly, it is hypothesized that vitamin D supplementation might prevent frailty.

Combined treatment with nandrolone decanoate, oral alphacalcidol (Vitamin $D_3$), and calcium supplementation in women recovering from hip fraction was shown to improve BMD, muscle mass and gait scores (Hedström et al. J Bone Joint Surg Br 2002; 84: 497-503). The document does not address frailty. Furthermore the subjects were living independently and had an average BMI status of 23 indicating that the subjects in this study were not frail. Whilst the study provides vitamin D in conjunction with the anabolic steroid, the disclosure, other than e.g. the Campbell et al. reference above, reflects the conventional wisdom in emphasizing the role of vitamin D in relation to bone, and the role of the anabolic steroid in relation to bone and muscle.

Efficient treatment of frailty symptoms is a real unmet medical need, given the way pathophysiology develops and associated health care cost increases.

In the alleviation and prevention of frailty symptoms, it is desired that more of the symptoms can be treated or prevented at the same time. In the treatment of frailty, it is desired to provide a single therapy that actually treats the condition, and particularly aims at improved functional capacity and independence, which are the preferred clinical end points for elderly patients. A typical consequence of frailty is that patients are subject to a downward spiral of decline, and will almost inevitably be headed towards admission into long-term care. It is desired to prevent and reverse the otherwise inevitable further decline and allow the patients to live independently for a longer period of time. This is particularly critical for patients that are in recovery after hospitalization, as this frequently is a turning point, in the frail elderly, leading to prolonged stays in a nursing homes (and further decline), rather than retaining independence (and regaining physical and mental activity, leading to improved health). Thus, medical intervention is needed.

SUMMARY OF THE INVENTION

In order to better address one or more of the foregoing desires, the invention, in one aspect is a method of treatment or prevention of frailty in an elderly patient, particularly having an age of 60 or older, comprising the concomitant parenteral administration of an effective dose of a combination of an anabolic steroid and a vitamin D compound.

In another aspect, the invention presents a composition comprising an anabolic steroid and a vitamin D compound for use in the treatment of frailty in an elderly patient, particularly having an age of 60 or older, comprising the concomitant parenteral administration of effective doses of an anabolic steroid and a vitamin D compound.

In a still further aspect, the invention is a pharmaceutical composition comprising an anabolic steroid and a vitamin D compound in a carrier liquid suitable for parenteral administration.

In yet another aspect, the invention includes an injection device for intramuscular administration of a liquid, wherein the liquid is a comprising an anabolic steroid and a vitamin D compound in a carrier liquid suitable for parenteral administration.

DETAILED DESCRIPTION OF EMBODIMENTS

Figure 1:
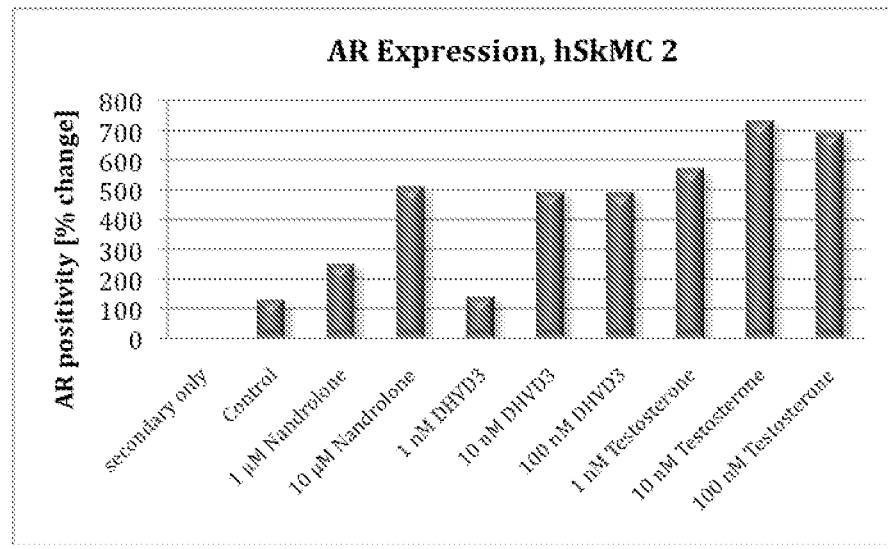
FIG. 1 is a bar diagram showing the effect of nandrolone and 1α,25-dihydroxyvitamin D3 (DHVD3) on the change in the percentage of cells with positive androgen (AR) receptor expression in human skeletal muscle cells (satellite cells), batch hSkMC2, after 5 days of treatment with nandrolone and/or DHVD3. Testosterone was used as reference.

The invention relates to the treatment of frailty. The term "frailty" is herein defined particularly with reference to the aforementioned definition (Fried et al. 2001). The patients to be treated will generally be elderly human, both male and female, usually having an age of 60 or older. More particularly, the patients treated are elderly having an age of 65 or older.

In a broad sense, the invention is based on the recognition that the current, piecemeal, studies oriented to individual symptoms of frailty are not sufficient to lead to an actual treatment. The invention addresses providing such a treatment by a specific administration route of a judicious combination of active substances. Without wishing to be bound by theory, the inventors believe that the efficacy of the combined parenteral administration of an anabolic steroid, preferably nandrolone decanoate, and a vitamin D compound, preferably vitamin D3 (cholecalciferol) is based on a synergistic effect between the two compounds, particularly on muscle mass and muscle function. This belief is based on the molecular action of the receptors for the two compounds and the pathways the two compounds may activate in myoblasts/satellite cells. Both the androgen receptor and the vitamin D receptor belong to the family of nuclear transcription factors, but their respective mode of action is quite different. The vitamin D receptor is known to be involved in cell proliferation and differentiation. The androgen receptor is involved in cell growth. In combination, therefore, they are believed to lead to a more optimal stimulation of muscle cell growth. Furthermore, the administration of an anabolic steroid, concomitantly with a vitamin D compound, is believed to positively affect vitamin D receptor activity. And vitamin D positively affects the neuromuscular system.

The invention involves the concomitant parenteral administration of effective doses of an anabolic steroid and a vitamin D compound. The term "concomitant administration" is well understood in the art, and generally refers to administration of two active substances at the same time, or almost at the same time. In the present invention this means that both of the compounds are administered within the same time interval. Thus, if one of the compounds is given daily, the other compound is also given daily, on the same day. If one of the compounds is given weekly, the other compound is also given weekly, in the same week. If one of the compounds is given monthly, the other compound is also given monthly, in the same month. It will be understood that the terms "day", "week" and "month" do not necessarily refer to a calender day, week, or month, but to the time intervals having the respective lengths. Preferably, both of the compounds are given directly after each other, and more preferably they are given simultaneously. Most preferably, the simultaneous administration is effected through one single composition comprising both of the compounds.

The term "parenteral administration" is well understood in the art, and generally refers to all routes of administration other than through the gastro-intestinal tract, including but not limited to intramuscular, intravenous, subcutaneous, transdermal, transmucosal, or inhalational administration. In the invention, the parenteral administration is preferably intramuscular or subcutaneous injection.

With a view to the patient group treated, the elderly, the most preferred administration route is by subcutaneous injection. The elderly are frequently characterized by having low muscle (particularly if suffering from frailty). On the other hand, they tend to have relative large skin, with many folds. Thus, especially in the treatment of frailty, subcutaneous injection has a particular advantage of being much easier, and less painful to the patient, than intramuscular injection.

The compounds are administered in effective doses. The term "effective dose" is well understood in the art. In pharmacology, effective dose is the median dose that produces the desired effect of a drug. The effective dose is often determined based on analysing the dose-response relationship specific to the drug. The dosage that produces a desired effect in half the test population is referred to as the ED-50, and this is generally recognized as an effective dose. In the context of the invention, the dose is considered to be effective if it serves to alleviate a plurality (i.e. two or more) of the symptoms of frailty. Preferred effective doses serve to treat the condition of frailty, as can be assessed trough suitable biomarkers and/or suitable clinical endpoints. In the context of the invention, the term "effective dose" relates to the combined dose of the two active substances. The effective dose, and the dose interval may sometimes be chosen differently among male and female patients. E.g. anabolic androgenic steroid doses can be higher in males. Further, females tend to suffer from frailty at a lower age than males, and may require a prolonged therapy of regular doses, whilst a male becoming frail at higher age may require a recovery boosting therapy of short duration and higher strength.

The combination of active substances of the invention comprises an anabolic steroid. The term "anabolic steroid" is well understood in the art as being a class of steroid hormones related to the hormone testosterone. For a review of anabolic steroids, reference is made to A. T. Kicman, British Journal of Pharmacology (2008) 154, 502-521. Anabolic steroids generally have overlapping anabolic and androgenic effects, and are therefore sometimes denoted anabolic-androgenic steroids (AAS). The androgenic:anabolic ratio of an AAS is an important factor when determining the clinical application of these compounds. It will be understood that in the present invention, it is desired that the anabolic (myotrophic) effect, which promotes the growth of muscle cells, takes precedence over the androgenic effect. In this respect, the anabolic steroid is preferably selected from the group consisting of norbolethone, oxymetholone, oxandrolone, oxymetholone, nandrolone, and esters thereof. The preferred anabolic steroid for use in the present invention is nandrolone or an ester thereof, most preferably nandrolone decanoate.

According to the invention, nandrolone decanoate is preferably administered (preferably by intramuscular injection and more preferably by subcutaneous injection) once monthly, more preferably once every three weeks, and most preferably weekly. The total dosage amount administered per time interval may generally vary from 15 mg, preferably 25 mg per month to 600 mg, preferably 400 mg per month. In the treatment of frailty according to the invention, it is preferred that the dose is not too low. In view of the inevitable androgenic effects it is also preferred that the dosage is not too high. Preferred dosages that are as low as possible, and as high as necessary, range per week from 5 mg, preferably from 10 mg to 150 mg, preferably 50 mg, or per month from 20 mg, preferably 40 mg to 600 mg, preferably 200 mg.

If another anabolic steroid is used, the preferred dosage ranges are equivalent with those mentioned for nandrolone decanoate. The person skilled in the art is aware of how to calculate the dosage conversions between various anabolic steroids.

The combination of active substances of the invention comprises vitamin D compound. In the context of the invention, the term "vitamin D compound" refers to vitamin D and the various forms thereof, as well as precursors and analogs of vitamin D. This class of compounds is well-known in the art. Preferably, the vitamin D compound is one of the common forms of vitamin D, and is selected from the group consisting of ergocalciferol, cholecalciferol, calcidiol, calcitriol, doxercalciferol, and calcipotriene. The most preferred form of vitamin D for use in the invention is cholecalciferol (vitamin $D_3$).

In the invention it is preferred to administer the vitamin D at a dosage strength leading to a plasma level above that associated with vitamin D deficiency. Vitamin D deficiency is generally defined as a 25-hydroxyvitamin D plasma concentration of less than 20 ng/mL (50 nmol/L). Plasma concentrations of >140 nmol/L have been associated with adverse effects. Therefore the preferred dosage of the vitamin D compound is selected so as to provide a plasma level of between 50 to 70 nmol/L and 140 nmol/L.

According to the invention, the preferred vitamin D compound cholecalciferol is preferably administered (most preferably by intramuscular injection) once monthly, more preferably once every three weeks, and most preferably weekly. The dosage for cholecalciferol ranges from the parenteral equivalent of an oral dose of 100-4000 IU/day or the corresponding doses per week or month. However, parenteral dosage amounts as high as 600000 IU (15 mg) cholecalciferol intramuscular are possible.

The aforementioned compounds are preferably comprised in a single pharmaceutical composition suitable for parenteral administration. More preferably this refers to a pharmaceutical composition comprising an anabolic steroid and a vitamin D compound, preferably the combination of nandrolone decanoate and cholecalciferol, in a carrier liquid suitable for parenteral administration. The carrier liquid preferably is an oil, more preferably selected from the group consisting of arachis oil, cottonseed oil, and sesame oil.

Without wishing to be bound by theory, the inventors believe that the fact that both the anabolic steroid and the vitamin D compound (and particularly both nandrolone decanoate and cholecalciferol) are oil-soluble, may contribute to a mutually beneficial effect on the stability of an oil-based injection preparation. Moreover, the combination, in a single injection preparation, of the two compounds facilitates the concomitant administration, is less invasive to the patient, and serves to address better compliance with the administration regimen of both of the drugs.

It will be understood that the pharmaceutical compositions of the invention may comprise further excipients as normally used in such preparations. Excipient, additives, adjuvants and the like for use in parenteral dosage forms are known to the skilled person, and do not require elucidation here.

In the treatment of frailty, the composition of the invention will generally be administered for a period of at least 3 months to 12 months, preferably for 4 to 8 months, and most preferably for 6 months. The invention provides a novel medical intervention in the treatment of frailty in elderly patients.

Whilst this treatment of frailty is without precedence the inventors believe (without wishing to be bound by theory), that the medical intervention of the invention has further benefits.

This particularly refers to the aforementioned turning point, at which an elderly patient, suffering from frailty, after hospitalization may no longer be able to retain his or her independence. Prolonged stays in nursing homes, also with proper physical and mental therapies, inherently deprives these patients of an important tool in preventing a downward spiral, viz. the independence of living their own lives, with regular day to day physical and mental activity.

In this respect the invention is based on the insight that adequate medical intervention in a patient at such a turning point, may not only treat the condition of frailty per se, but serves to support the patient in retaining independence, and regaining physical and mental activity. In order to thus support these patients towards an improved health, the invention also provides a recovery booster therapy for frail elderly people, particularly after hospitalization or surgery. In this aspect of the invention, a relatively high dosage of the two active substances, preferably nandrolone decanoate and cholecalciferol, is administered at a relatively high frequency, preferably weekly, for a period of time that is long enough to provide the required pharmacological action, yet short enough to be felt as a short-term booster therapy (to regain independence) rather than permanent medication (which would reflect chronic illness). A preferred duration of the booster treatment is 4-8 months, preferably 6 months.

The invention also relates to the prevention of frailty in patients that are prone to become frail after hospitalization. Generally, these patients will be beyond a state of sarcopenia, and suffer from a reduced immune function.

It is preferred that the aforementioned booster therapy be conducted using, upon each administration, a single pharmaceutical composition comprising both of the compounds.

Devices for the parenteral administration of the compounds used in the invention are known to the skilled person. Based on known hardware, such, the invention also pertains to an injection device for intramuscular administration of a liquid, wherein the liquid is a composition in accordance with the invention, as described above.

The invention is further illustrated hereinafter with reference to the following, non-limiting examples, and the accompanying figures.

The examples are in vitro studies which demonstrate that nandrolone and 1α,25-dihydroxyvitamin D3 have a synergistic effect on muscle satellite cell proliferation and thus on muscle mass. The invention accordingly aims at lower doses of nandrolone decanoate used in humans in order to achieve the same effect on muscle mass and/or function with the combination as with nandrolone decanoate alone. This serves to address a better safety profile.

EXAMPLE 1

Materials and Methods

Two different batches of human skeletal muscle cells or satellite cells (hSkMC1—obtained from a 33 year old healthy female—and hSkMC2—obtained from a 64 year old healthy female) were obtained from PromoCell (Heidelberg, Germany) and cultured in flasks according to the instructions by the provider. Cells were harvested and stored in liquid nitrogen until used for the experiments. Cells were not used at passage number higher than 15. For the experiments cells were cultured at 37° C. and 5% CO2 at a density of 3,500-7,000 cells/cm2 in basal medium (PromoCell) plus the addition of 5% charcoal (Sigma-Aldrich) treated fetal bovine serum (FBS) (PAA, Germany) using 24-well plates (Costar) til about 80% confluency. Nandrolone, testosterone and 1α,25-dihydroxyvitamin D3 were purchased from Sigma-Aldrich.

For receptor studies the cells were cultured for 5 days with the addition of 1 μM and 10 μM nandrolone (the active metabolite of nandrolone decanoate) or 1, 10 and 100 nM 1α,25-dihydroxyvitamin D3. Androgen and vitamin D receptor staining protocols with the subsequent visualization by flow cytometry methods were derived from the publications of Krishan et al. (2000) and Folgueira et al. (2000). The method that yielded the best staining patterns included formalin-fixation followed by Tween 20 permeabilization and double staining with unlabeled primary antibodies (anti-androgen receptor (Epitomics) and anti-vitamin D receptor (GeneTex) and fluorophore labeled secondary antibodies (goat anti-rat IgG, PE-conjugated for staining the vitamin D receptor and goat anti-rabbit, FITC-conjugated for staining the androgen receptor both from Rockland). The staining with the two secondary antibodies only was used as background. The Fc-receptors were blocked by incubation with serum-containing buffer. All solutions further contained Tween 20 (Sigma Aldrich) as detergent to maintain the permeabilized status of the cells throughout the entire staining experiment. The staining in non-stimulated and stimulated cells were compared by determining the intensity of the staining in the cells as well as the staining in the % of cells. The measurements were performed with a dual color flow cytometer (Beckman Coulter type FC500 Cytomics). The increase in the % of stained cells beyond the setpoint of the marker (at 1% for background staining) was determined with and without hormonal treatment.

For proliferation studies the cells were cultured for 8 days with 100 and 1000 nM nandrolone alone or 10 and 100 nM 1α,25-dihydroxyvitamin D3 and the combinations of nandrolone and 1α,25-dihydroxyvitamin D3. Medium and hormones were replaced on day 1, 4 and 7. Proliferation was measured using the resazurin assay (Stern-Straeter et al., 2008). Statistical analysis of the proliferation data was performed with the Student's t-test.

EXAMPLE 2

Receptor Studies

Figure 2:
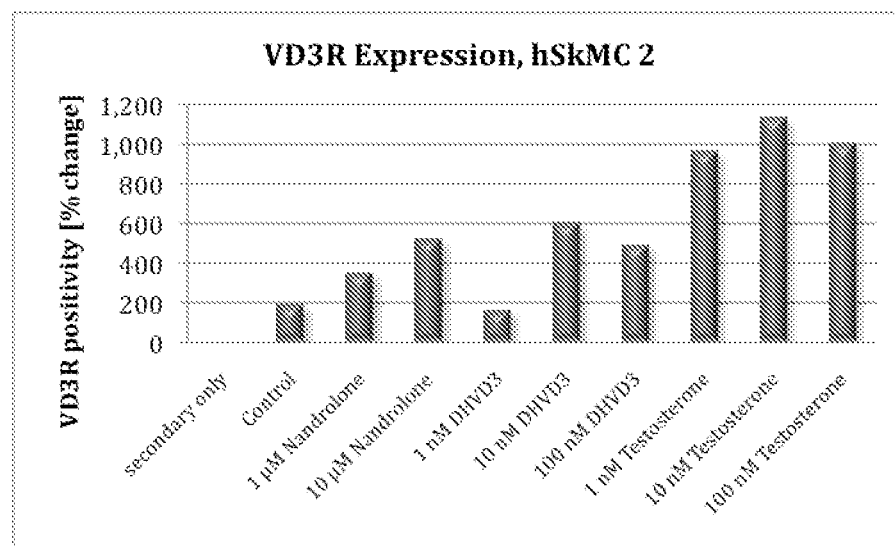
FIG. 2 is analogous to FIG. 1, showing the effects on positive vitamin D receptor (VD3R) expression.

The action of both nandrolone and 1α,25-dihydroxyvitamin D3 on cells is dependent on the presence of their cognate receptors. We therefore investigated the presence of both the androgen and vitamin receptor in the used human skeletal muscle cells. FIGS. 1 and 2 shows the effect of nandrolone and 1α,25-dihydroxyvitamin D3 on the percentage of cells in which the expression androgen and vitamin D receptor changes compared to staining with secondary antibody alone. In the hSkMC2 cells increases in the number of cells with positive androgen and vitamin D receptor are observed after exposure to nandrolone as well as to 1α,25-dihydroxyvitamin D3. The histograms show also an increase in the intensity of the staining in the cells, which indicates an increase of the number of receptors per cell, when they contained already the receptor before hormone treatment. These results indicate that more cells become androgen receptor positive and that also the number of receptors per cell increase when they were receptor positive before treatment. The effects in hSkMC1 cells were less pronounced (data not shown).

These receptor studies show that both the androgen and the vitamin D receptor are present in human skeletal muscle cells and that nandrolone and 1α,25-dihydroxyvitamin D3 stimulate expression of each others' receptor.

EXAMPLE 3

Proliferation Studies

The increase in the percentage androgen receptor and vitamin D receptor positive cells by the two compounds as shown in Example 1 indicates that more cells potentially can respond to the treatment.

The proliferation of human skeletal muscle cells was used as a response parameter in order to test whether the combination of nandrolone and 1α,25-dihydroxyvitamin D3 has a synergistic effect on muscle mass.

Figure 3:
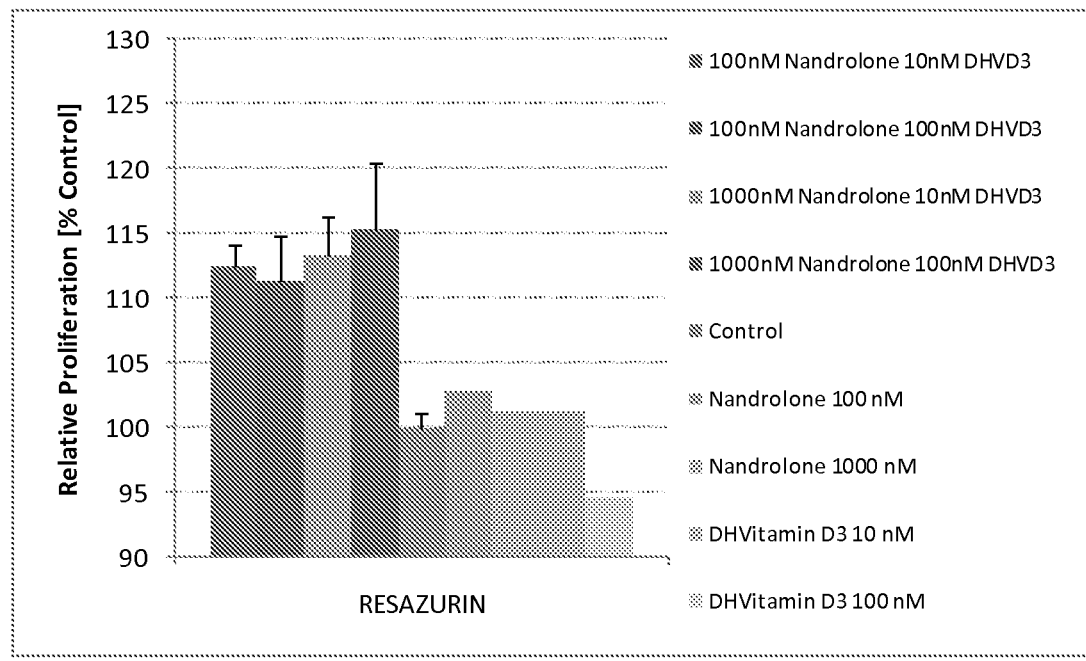
FIGS. 3(a) and (b) are bar diagrams showing the effect of two concentrations of nandrolone and 1α,25-dihydroxyvitamin D3 (DHVD3) alone and that of their combinations on the proliferation of human skeletal muscle cells (batches hSkMC1 and 2) which is used as a measure for muscle mass.
Figure 3:
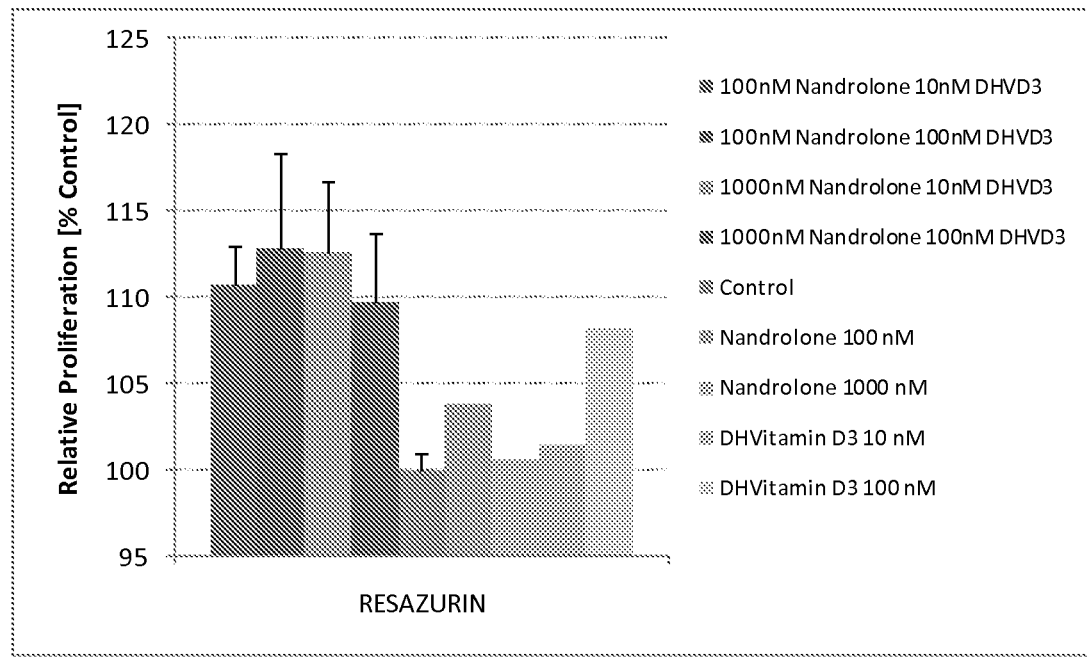

FIG. 3 shows (a) for hSkMC1 cells no effect on proliferation by the individual compounds, but when 1α,25-dihydroxyvitamin D3 was combined with nandrolone a significant effect was seen for all 4 combinations tested ($P<0.001$ except for 100 nM nandrolone plus 100 nM 1α,25-dihydroxyvitamin D3, which is significant at $P<0.05$). For (b) hSkMC2 cells the higher concentrations of 1α,25-dihydroxyvitamin D3 show an increase in proliferation and again the 4 combinations show a significant effect compared to control ($P<0.05$ except for 100 nM nandrolone plus 10 nM 1α,25-dihydroxyvitamin D3, which is significant at $P<0.001$). The percentage increases over control for the various treatments are presented in Table 1 below. For hSkMC1 cells the increases for all combinations exceed the sum of the increases for the individual compounds in the combination. This proves the synergistic effect of the combination of nandrolone plus 1α,25-dihydroxyvitamin D3 on human skeletal muscle cells. For hSkMC2 cells synergistic effects are observed in three out of the four tested combinations.

TABLE 1

Percentage increase (% Δ) in proliferation of human skeletal muscle cells (hSkMC1 and hSkMC2) by nandrolone and 1α,25-dihydroxyvitamin D3 (dhvit D3) alone and combinations of the two compounds compared to control.

|  | hSkMC1 | | hSkMC2 | |
| --- | --- | --- | --- | --- |
|  | % Δ | Σ | % Δ | Σ |
| 100 nM nandrolone | 3 |  | 4 |  |
| 1000 nM nandrolone | 1 |  | 1 |  |
| 10 nM dhvit D3 | 1 |  | 1 |  |
| 100 nM dhvit D3 | −5 |  | 8 |  |
| 100 nM nandrolone + 10 nM dhvit D3 | 12 | 4 | 11 | 5 |

TABLE 1-continued

Percentage increase (% Δ) in proliferation of human skeletal muscle cells (hSkMC1 and hSkMC2) by nandrolone and 1α,25-dihydroxyvitamin D3 (dhvit D3) alone and combinations of the two compounds compared to control.

|  | hSkMC1 | | hSkMC2 | |
|---|---|---|---|---|
|  | % Δ | Σ | % Δ | Σ |
| 100 nM nandrolone + 100 nM dhvit D3 | 11 | −2 | 13 | 12 |
| 1000 nM nandrolone + 10 nM dhvit D3 | 13 | 2 | 13 | 2 |
| 1000 nM nandrolone + 100 nM dhvit D3 | 10 | −4 | 15 | 9 |

Σ represents: the sum of % Δ of nandrolone alone plus the % Δ of dhvit D3 alone as used in the various combinations.

The invention claimed is:

1. A pharmaceutical composition which contains 5 mg to 50 mg nandrolone decanoate, and 17.5 μg to 15 mg of cholecalciferol consisting of:
   (i) active substances consisting of nandrolone decanoate and cholecalciferol in a molar ratio of 100:1 to 1:1; and
   (ii) a carrier liquid suitable for parenteral administration wherein the molar ratio of nandrolone decanoate and cholecalciferol results in a synergistic increase in muscle mass in a subject when said composition is administered to said subject.

2. The pharmaceutical composition according to claim 1, wherein the carrier liquid is selected from the group consisting of arachis oil, cottonseed oil, and sesame oil.

3. The pharmaceutical composition according to claim 1, wherein the carrier liquid is an oil.

4. The pharmaceutical composition according to claim 1, wherein the carrier liquid is suitable for subcutaneous administration.

5. A method of treatment of frailty in an elderly patient comprising administering the pharmaceutical composition of claim 1.

6. The method according to claim 5, wherein the administering is done at least monthly.

7. The method according to claim 5, wherein the administering is done for a period of at least 3 months.

8. The method according to claim 5, wherein the patient has an age of 60 or older.

9. The method according to claim 6, wherein the administering is done at least weekly.

10. The method according to claim 7, wherein the administering is done for a period of 3 to 12 months.

11. The method according to claim 8, wherein the patient has an age of 65 or older.

12. The method according to claim 5 wherein said treatment increases muscle mass.

* * * * *